(12) United States Patent
Reisman et al.

(10) Patent No.: US 9,107,610 B2
(45) Date of Patent: Aug. 18, 2015

(54) OPTIC NEUROPATHY DETECTION WITH THREE-DIMENSIONAL OPTICAL COHERENCE TOMOGRAPHY

(71) Applicant: Kabushiki Kaisha TOPCON, Tokyo (JP)

(72) Inventors: Charles A. Reisman, Mamaroneck, NY (US); Qi Yang, Morris Plains, NJ (US)

(73) Assignee: KABUSHIKI KAISHA TOPCON, Tokyo (JP)

( * ) Notice: Subject to any disclaimer, the term of this patent is extended or adjusted under 35 U.S.C. 154(b) by 0 days.

(21) Appl. No.: 14/071,745

(22) Filed: Nov. 5, 2013

(65) Prior Publication Data

US 2014/0152957 A1 Jun. 5, 2014

Related U.S. Application Data

(60) Provisional application No. 61/731,829, filed on Nov. 30, 2012.

(51) Int. Cl.
*A61B 3/14* (2006.01)
*A61B 3/10* (2006.01)
*G06T 7/00* (2006.01)

(52) U.S. Cl.
CPC .............. *A61B 3/102* (2013.01); *G06T 7/0012* (2013.01); *G06T 2207/10101* (2013.01); *G06T 2207/30041* (2013.01)

(58) Field of Classification Search
CPC ........ A61B 3/102; A61B 3/14; A61B 5/0066; G06T 2207/10101; G06T 2207/30041; G06T 7/0081; G06K 9/0014; G01B 9/02027; G01B 9/02091

USPC .......... 351/205, 206, 221; 356/450, 451, 456, 356/477, 479; 382/131; 600/407, 425
See application file for complete search history.

(56) References Cited

U.S. PATENT DOCUMENTS

| 2011/0149291 | A1* | 6/2011 | Yamakita ..................... 356/450 |
| 2012/0274897 | A1* | 11/2012 | Narasimha-Iyer et al. ... 351/206 |
| 2013/0222767 | A1* | 8/2013 | Cheng et al. .................. 351/246 |

OTHER PUBLICATIONS

Choi, Yun Jeong et. al "Glaucoma Detection Ability of Ganglion Cell-Inner Plexiform Layer Thickness by Spectral-Domain Optical Coherence Tomography in High Myopia" In: Investigative Ophthalmology & Visual Science, Mar. 2013, vol. 54, No. 3, p. 2296-2304.
Mwanza, Jean-Claude et al. "Macular Ganglion Cell—Inner Plexiform Layer: Automated Detection and Thickness Reproducibility with Spectral Domain—Optical Coherence Tomography in Glaucoma" In: Investigative Ophthalmology & Visual Science, Oct. 2011, vol. 52, No. 11, p. 8323-8329.
Wojkowski, Maciej et. al. "Three-dimensional Retinal Imaging wiht High-Speed Ultrahigh-Resolution Optical Coherence Tomography" In: Ophthalmology by the American Academy of Ophthalmology 2005, vol. 112, pp. 1734-1746.

(Continued)

*Primary Examiner* — Mahidere Sahle
(74) *Attorney, Agent, or Firm* — Pearne & Gordon LLP

(57) ABSTRACT

Based on optical coherence tomography (OCT) imaging of a portion of an eye, a mask of an anatomical feature is derived. Using the mask as a reference, a scan path is determined that is at least partially fitted to and/or partially enclosing the mask. OCT scan data corresponding to the scan path is acquired and analyzed to detect optic neuropathies.

35 Claims, 8 Drawing Sheets

(56) References Cited

OTHER PUBLICATIONS

Blumenthal, Eytan Z. "Quantifying Retinal Nerve Fiber Layer Thickness Histologically: A Novel Approach to Sectioning of the Retina" In: Investigative Opthalmology & Visual Science, May 2004, vol. 45, No. 5. pp. 1404-1409.

Carpineto, P. et. al. "Custom measurement of retinal nerve fiber layer thickness using SRATUS OCT in normal eyes" In: European Journal of Opthalmology, vol. 15 No. 3 2005, pp. 360-366.

Patel, Nimesh B. et. al. "Retinal Nerve Fiber Layer Assessment: Area versus Thickness Measurements from Elliptical Scans Centered on the Optic Nerve" In: Investigate Opthalmology & Visual Science, Apr. 2011, vol. 52, No. 5. pp. 2477-2489.

Singh, Amardeep S.G. et. al. "Stable absolute flow estimation with Doppler OCT based on virtual circumpapillary scans" In: Biomedical Optics Express Nov. 1, 2010, vol. 1, No. 4. pp. 1047-1059.

Savini M.D., Giacoma et. al. "The Effect of Scan Diameter on Retinal Nerve Fiber Layer Thickness Measurement Using Stratus Optic Coherence Tomography" In: Arch Opthhalmol Jul. 2007, vol. 128, No. 7, pp. 901-905.

Cyl, Cheung et. al. "Effects of scan circle displacement in optical coherence tomography retinal nerve fibre layer thickness measurement: a RNFL modelling study" In: Eye 2009, vol. 23, pp. 1436-1441.

Stein, DAniel M. et. al. "Imaging in glaucoma" In: NIH Public Access Author Manuscript Ophthalmol Clin North Am., Mar. 2004, vol. 17 (1), pp. 33-52.

Teesalu, Pait et. al. "Optical coherence tomography and localized defects of the retinal nerve fiber layer" In: Acta Ophthalmologica Scandinavica 2000, vol. 78, pp. 49-52.

Carpineto M.D., Paolo et. al. "Reliability of Nerve Fiber Layer Thickness Measurements Using Optical Coherence Tomography in Normal and Glaucomatous Eyes" In: Ophthalmology by the American Academy of Ophthalmology 2003, vol. 110. pp. 190-195.

Schuman, Joel S. et. al. "Quantification of Nerve Fiber Layer Thickness in Normal and Glaucomatous Eyes Using Optical Coherence Tomography" In: Arch Ophthalmol. May 1995, vol. 113, pp. 586-596.

Leung, MD, Christopher K. S. et. al. "Retinal Nerve Fiber Layer Imaging with Spectral-Domain Optical Coherence Tomography" In: Ophthalmology by the American Academy of Ophthalmology 2010, vol. 117, pp. 1684-1691.

* cited by examiner

OPTIC NEUROPATHY DETECTION WITH THREE-DIMENSIONAL OPTICAL COHERENCE TOMOGRAPHY

CROSS-REFERENCE TO RELATED APPLICATIONS

This application claims priority to U.S. Provisional Application Ser. No. 61/731,829, filed on Nov. 30, 2012, entitled "OPTIC NEUROPATHY DETECTION WITH THREE-DIMENSIONAL OPTICAL COHERENCE TOMOGRAPHY BASED ON A FITTED ANNULUS", the entirety of which is incorporated herein by reference.

BACKGROUND OF THE INVENTION

1. Field of the Invention

This application relates generally to optical diagnostic methods and apparatus and, more specifically, to an optic neuropathy detection method and apparatus utilizing optical coherence tomography.

2. Description of Related Art

Conventional diagnostics for eye disorders typically include a detailed ophthalmic examination of the retina. For initial examination, an eye doctor will view the retina through an ophthalmoscope. For a permanent record, the retina is typically photographed with a fundus camera. A fundus photograph directly records various anatomical features of the retina, such as the optic disc, fovea, blood vessels, and lesions. The imaging capabilities of fundus photography may be enhanced by supplementary techniques. A high-contrast image of retinal blood vessels, for example, may be photographed after the injection of a fluorescent dye into the bloodstream. The resulting image is referred to as a fluorescein angiogram.

More sophisticated techniques have been developed for diagnostics of the eye. One such technique is three-dimensional optical coherence tomography (3D OCT). In this technique, a light beam is directed onto the retina. Part of the beam is back-reflected, and interferometric analysis of the back-reflected light yields information on the structure of the retina. By varying optical parameters of the light probe, features at different depths below the surface of the retina may be analyzed. With this process, an image of a cross-section of the retina may be generated by scanning the optical probe along a line on the retina. By rastering the optical probe across the surface of the retina, a series of cross-sectional images may be produced. The series of cross-sectional images may be used to characterize the 3D structure of the retina, and parameters such as local retinal thickness may be measured by 3D OCT.

Analysis of the thickness of the retina, or a portion of the retina, may be used to diagnose certain diseases of the eye, such as glaucoma. Different portions of the retina may be analyzed, including the retinal nerve fiber layer, the ganglion cell layer, the ganglion cell complex or the like. One indication of the health of the eye may be provided by comparing the retinal thickness of the patient's eye with reference data acquired from a population of healthy eyes. Progression of eye disease may also be monitored by measuring changes in retinal thickness over a period of time.

For example, a conventional approach is to utilize a circumpapillary scan to detect glaucoma and monitor a progression of glaucoma in a patient. A circle scan is performed around the optic disc at a fixed diameter. From the scan data, a thickness of the retinal nerve fiber layer around the circle is measured. However, as optic disc sizes vary from patient to patient, the fixed circle diameter needs to be sufficiently large enough to encompass the optic discs of all patients. Thus, the circle is arbitrarily sized substantially larger than the optic disc sizes of most patients. This results in useful information, which is acquired close to the optic disc, being missed. Further, when attempting to utilize circles with smaller diameters, the circle scans clip the optic disc of some patients.

BRIEF SUMMARY OF THE INVENTION

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

In various, non-limiting embodiments, a substantially annular region is at least partially fitted around an anatomical marker in a region of interest of a patient's eye. In one example, the substantially annular region is determined based on 3D OCT data of the region of interest of the patient's eye. The substantially annular region can be scanned, virtually or directly, to acquire OCT information particular to the substantially annular region. Various measurements, taken from the OCT information of the substantially annular region, are aggregated and/or integrated. Such measurements are employed along with various clinical, analytical, and/or statistical techniques to facilitate diagnosis and monitoring of optic neuropathies.

These and other embodiments are described in more detail below.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
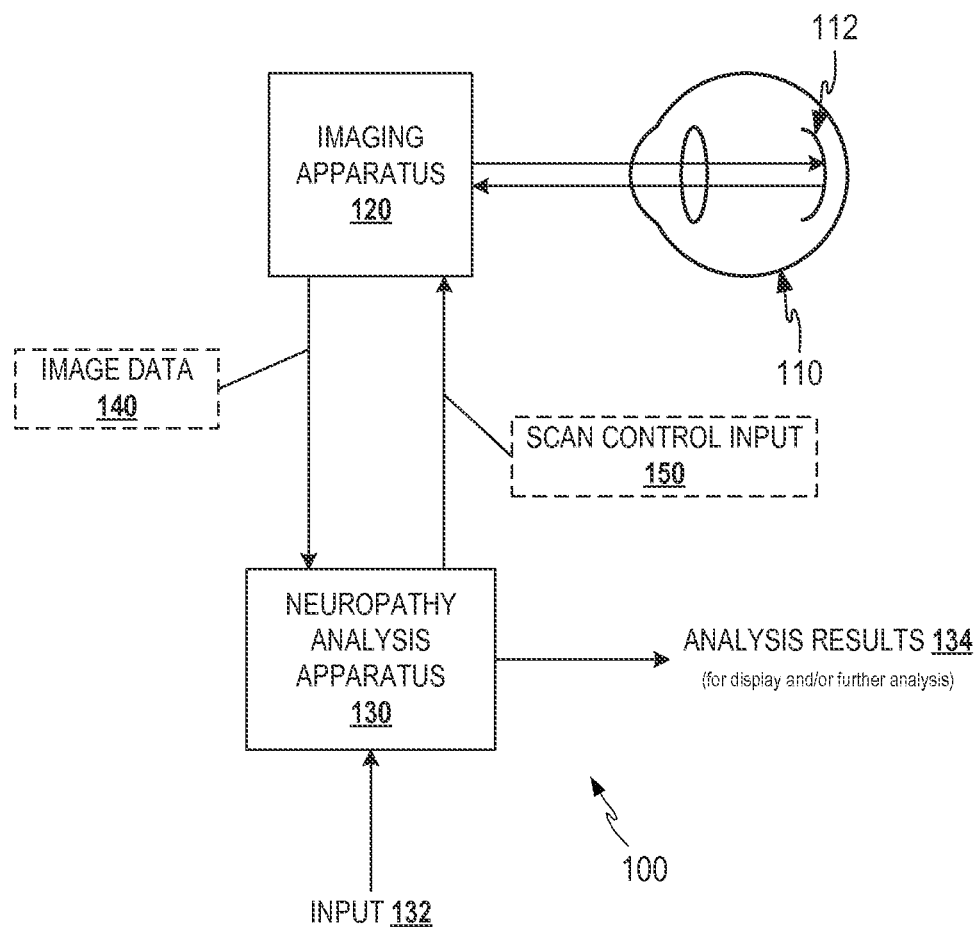
FIG. 1 illustrates an exemplary, non-limiting system for detecting and measuring optic neuropathies of an eye.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

As used herein, the terms "annular region" and "substantially annular region" mean a ring-shaped area that is bounded by an outer perimeter and an inner perimeter. The outer and inner perimeters may be circular in shape, but may alternatively take any other suitable shapes, including but not limited to an elliptical shape, a polygonal shape, or any suitable, regular or irregular shape.

Diseases such as glaucoma, multiple sclerosis, etc., present as an optic neuropathy in which nerve tissue in a retina of an eye is destroyed. Various techniques are available to diagnose and monitor optic neuropathies (e.g., pressure estimates within the eye, visual field (VF) tests, optic head analyzers that measure cup-to-disc ratio, etc.). Optical coherence tomography (OCT), however, is shown to enable early detection and fine measurements of disease progression while requiring less effort and strain for the subject as compared to VF testing and appears to have greater repeatability. Further, OCT generally allows for a denser sampling of the retina, particularly within the macula, than some types of VF testing.

According to one or more aspects described herein, OCT imaging is selectively acquired and/or analyzed based on characteristics of diseases that present as optic neuropathies and specific characteristics of a subject's anatomy. For instance, based on imaging of the subject's anatomy, a customized scan path can be determined and/or specific portions of OCT imaging data can be extracted. The customized scan path and/or the specific portions correspond to diagnostically relevant regions of the subject's anatomy. From the OCT imaging data acquired through extraction or scanning of the scanning path, diagnostically relevant measurements are obtained.

In one embodiment, a method for optical coherence tomography (OCT) imaging is described herein. The method includes obtaining imaging data of a region of interest of a subject, the region of interest including at least one anatomical marker; generating a mask of the anatomical marker based on the imaging data; determining a scan path based at least in part on the mask, the scan path traversing at least a portion of an arbitrary enclosing shape at least partially fitted around the mask; and acquiring three-dimensional optical coherence tomography (3D OCT) scan data corresponding to the scan path.

According to one example, acquiring the 3D OCT scan data corresponding to the scan path further comprises directly scanning the scan path with an OCT imaging apparatus. In another example, obtaining the imaging data further comprises performing a 3D OCT scan of the region of interest including the anatomical marker. Further to this example, acquiring the 3D OCT scan data corresponding to the scan path further comprises performing a simulated scan from results of the 3D OCT scan of the region of interest including the anatomical marker. Performing the simulated scan can include extracting data from the 3D OCT scan data within the scan path. The data extracted are a plurality of A-scans from the 3D OCT scan data within an area of the region of interest covered by the scan path. In addition, the method can include generating a simulated B-scan from the plurality of A-scans.

In yet another example, the method can also include acquiring at least one measurement from the 3D OCT scan data corresponding to the scan path. The measurement is at least one of a layer thickness, an attenuation coefficient, or an image-derived coefficient. The measurement acquired from the 3D OCT scan data could be a combined measurement, such as an integrated attenuation coefficient which is a combination of the layer thickness and the attenuation coefficient. In another example, the measurement is an atrophic measure indicating a percentage of an area of the scan path in which peripapillary atrophy is detected. The region of interest can be a retina and the anatomical marker can be an optic disc such that acquiring the at least one measurement includes measuring a characteristic of at least a nerve fiber layer of the retina within the scan path. However, the anatomical marker could also be a fovea such that acquiring the at least one measurement includes measuring a characteristic of a ganglion cell layer of the retina within the scan path. In either situation, when the region of interest is the retina, acquiring the at least one measurement comprises measuring the characteristic over one layer or a combination of layers of retina, the layers including at least one of: a ganglion cell layer and an inner plexiform layer; a nerve fiber layer, the ganglion cell layer, and the inner plexiform layer; or all retinal layers (frequently referred to as "total retinal thickness"). The at least one measurement can be compared to a normative database.

Further still, the method can include displaying information derived from at least one of the at least one measurement, the imaging data, or the 3D OCT scan data. For instance, displaying the information can include displaying a visual representation of measurement results as an overlay on an OCT-derived image. According to other examples, the arbitrary enclosing shape is a substantially annular shape. An inner dimension of the substantially annular shape corresponds to a margin of the mask. Also, the scan path comprises one or more sub-sections of the substantially annular shape. The one or more sub-sections can be discontinuous. In general, determining the scan path further comprises selecting a first enclosing shape, aligning the first enclosing shape with the mask, and adjusting at least one dimension of the first enclosing shape such that a minimum value of the at least one dimension is greater than or equal a dimension of a margin of the mask.

According to another embodiment, a method for detecting optic neuropathies from OCT imaging data is described. The method can include acquiring imaging data of a region of a retina that includes an optic disc; determining an optic disc mask based on the imaging data; determining a scan path based at least in part on the optic disc mask, wherein the scan path comprises one or more sub-paths, the one or more sub-paths being positioned based in part on an outer dimension of the optic disc mask; and acquiring 3D OCT scan data corresponding to the scan path. In one example, the one or more sub-paths traverse a minimally fitted annular shape having an inner dimension corresponding to the outer dimension of the optic disc mask. According to another example, obtaining the imaging data can include performing a 3D OCT scan of the region of the retina including the optic disc. In yet another example, acquiring the 3D OCT scan data corresponding to the scan path can include performing a simulated scan from results of the 3D OCT scan of the region of the retina including the optic disc. According to further examples, the method can include acquiring at least one measurement value from the 3D OCT scan data corresponding to the scan path. The method can also include displaying information derived from at least one of the at least one measurement value, the imaging data, or the 3D OCT scan data.

In yet another embodiment, an OCT imaging system is described herein. The OCT imaging system includes an imaging apparatus for capturing OCT scan data of a region of interest of a subject, the region of interest including at least one anatomical marker. The OCT imaging system can also include a neuropathy analysis apparatus for processing the OCT scan data to output analysis results relevant to diagnosis of optic neuropathies. The neuropathy analysis apparatus is configured to generate a mask for the anatomical marker based on image processing of the OCT scan data; determine a scan path based at least in part on the mask, the scan path traversing at least a portion of an arbitrary enclosing shape at least partially fitted around the mask; extract portions of the OCT scan data corresponding to the scan path; aggregate measurement values, relative to at least one characteristic of the region of interest, over the portions of the OCT scan data extracted; and output, as the analysis results, information derived from at least one of the measurement values aggregated or the portions of the OCT scan data extracted. According to an example, the neuropathy analysis apparatus is further configured to receive input, the input specifies at least one of a size and location of the arbitrary enclosing shape, one or more sub-regions of the arbitrary enclosing shape included in the scan path, or a width of the arbitrary enclosing shape. In yet another example, the neuropathy analysis apparatus is further configured to control the imaging apparatus to directly capture imaging data corresponding to the scan path.

FIG. 1 illustrates an exemplary, non-limiting system 100 for detecting and/or measuring optic neuropathy in an eye 110. Particularly, system 100 includes an imaging apparatus 120 configured to generate image data 140 corresponding to a region of interest 112 of the eye 110, such as the retina or a portion thereof for example. According to one example, the region of interest 112 can be an optic disc of the eye 110 in order to detect optic neuropathy associated with glaucoma. In another example, imaging apparatus 120 scans a macula of the eye 110 as the region of interest to facilitate detection and/or monitoring of glaucoma, multiple sclerosis, macular degeneration, etc.

In accordance with an example, imaging apparatus 120 can be an OCT apparatus and will generally be discussed as such to facilitate explanation of aspects provided herein. However, it is to be appreciated that the subject matter is not limited to application only with OCT and that the aspects described herein can be utilized in connection with other imaging modalities such as, but not limited to, computed tomography (CT), magnetic resonance imaging (MRI), ultrasound, etc.

OCT is an imaging technique capable of acquiring sub-surface images of a subject at micrometer resolutions. For instance, in ophthalmological applications, OCT is utilized to generate cross-sectional images of portions of an eye, including the retina. In general, OCT operates according to the same basic principles as ultrasound but utilizes light as a medium whereas ultrasound utilizes sound. That is, OCT images the subject by irradiating the subject with light and measuring a time delay and intensity of reflected light. However, light is much faster than sound. So, unlike the time delay in an ultrasound echo, the time delay of the reflected light is not directly measured. Instead, OCT utilizes low-coherence interferometry to detect time differences corresponding to distances between structures of the subject. Particularly, a low-coherence broadband light source is split into a sample portion and a reference portion. The reference portion travels a path toward a reference (i.e., a reference mirror) while the sample portion is directed towards the subject (e.g., an eye and, specifically, the retina). When a distance traveled by the sample portion and a corresponding reflection off the subject is within a coherence length of a distance traveled by the reference portion and its corresponding reflection, an interference pattern is generated. The interference pattern indicates an intensity of light at a certain depth of the subject, which in turn, facilitates generating image data pertaining to the subject.

To derive intensity information at varying depths of the subject, several different techniques can be utilized. In one technique, referred to as time-domain OCT, the travel distance of the reference portion is modulated to scan different depths. For example, the reference mirror can be oscillated to change the travel distance. Other techniques, which can be collectively referred to as frequency-domain OCT, do not require alterations to the reference portion. In these techniques, various frequencies of light can be encoded, spatially or temporally for example, where different detected frequencies of reflected light correspond to different depths within the subject. A Fourier analysis on a received signal that represents reflected intensities at different frequencies generates the intensities reflected at different depths at a point of the subject.

According to one example of a frequency-domain OCT technique (commonly referred to as Fourier-domain or spectral-domain OCT), a reference interference pattern is dispersed into individual frequency components by a grating or other such dispersive means. Conceptually, an array of photodetectors, each sensitive to a specific range of frequencies, simultaneously detects respective intensities of the frequency components corresponding to different depths at a scanned point of the subject. In conventional practice, however, typically a charge couple device (CCD) or complimentary metal-oxide-semiconductor (CMOS) line camera or spectrometer is utilized and the grating physically separates the different wavelengths of light. In another example, referred to as swept-source OCT, a tunable light source is utilized to scan over different frequencies. The intensities at each scanned frequency can be collected and transformed by a Fourier analysis to generate an intensity profile that details intensities at various depths.

A plurality of points or locations of the region of interest 112 can be scanned by the imaging apparatus 120 to generate a plurality of corresponding A-scans. Each A-scan provides a respective intensity profile within the region of interest 112 at the corresponding location. A series of A-scans can be assembled to collectively form a cross-sectional image of the region of interest 112, which is also known as a B-scan. For instance, A-scans associated with points along some arbitrary path on the region of interest 112 can be aggregated to generate a cross-sectional image, along the arbitrary path, of the region of interest 112. According to one embodiment, the imaging apparatus 120 is directed to physically scan the region of interest 112 along the arbitrary path to acquire the A-scans. In another embodiment, however, the imaging apparatus 120 acquires A-scans for an area of the region of interest 112 (such as an entirety thereof) that contains the arbitrary path. Subsequently, a B-scan along the arbitrary path can be extracted from the A-scan information. The B-scan, generated using this technique, can be referred to as a virtual or simulated scan since the imaging apparatus 120 is not directly scanning the arbitrary path.

A plurality of B-scans, along parallel cross-sections for instance, can be assembled to provide a three-dimensional (3D) scan image of the volume of the region of interest 112. Various slices of the 3D scan image can be computed and are typically referred to as C-scans. For example, C-scans corresponding to en face images of retinal layers or of the fundus of the eye 110 can be computed from the 3D scan image (or 3D scan data underlying the 3D scan image).

As utilized herein, 3D scan data can refer to a set of A-scans for a region of interest, one or more B-scans derived from A-scans of the set, one or more C-scans derived from the A-scans and B-scans, or the like. In an aspect, image data 140, provided to a neuropathy analysis apparatus 130 by the imaging apparatus 120, can be 3D scan data. It is to be appreciated that image data 140 can also include supplementary information in addition to the 3D scan data. For example, the imaging apparatus 120 can be capable of acquiring a fundus image in addition to OCT image data. In such cases, the fundus image can be acquired by scanning laser ophthalmoscopy, a fundus camera, or the like. However, it is to be appreciated that the fundus image can be generated from the 3D scan data by, for instance, summing every pixel in every A-scan.

From image data 140, and particularly the 3D scan data included therein, various measurements and quantifications can be determined. As discussed above, in ophthalmology, layer thickness, as measured in an axial direction, is a commonly utilized measurement to diagnose diseases that present as an optic neuropathy as well as to monitor progression of such diseases. Accordingly, neuropathy analysis apparatus 130 is configured to evaluate image data 140, calculate measurements, and output analysis results 134 for display and/or further analysis.

Taking glaucoma as an exemplary disease that presents as an optic neuropathy, increased pressure and/or tension within the eye can cause nerve fiber axons to kink and die, usually in association with anatomical or morphological changes to the Lamina Cribrosa, and/or can cause ganglion cells to die. Thus, over time, glaucoma causes atrophy in the nerve fiber layer (NFL), the ganglion cell layer (GCL), and the inner plexiform layer (IPL). Typically, NFL damage assumes the form of an arcuate shape centered on an optic disc of the eye and extending to a more temporal location, relative to the optic disc. GCL damage is often seen as a ring or a portion of a ring centered on the macula of the eye. The NFL and GCL damage typically presents as a thinning of the layers in the respective areas. Attenuation characteristics appear to be affected by such damage (attenuation is reduced in diseased tissue), particularly with respect to the NFL.

Conventionally, a circumpapillary scan technique is utilized to detect glaucoma and monitor a progression of glaucoma in a patient. In this conventional approach, a circle scan is performed around the optic disc at a diameter of approximately 3.4 mm (specifically, in the range of 3.0 to 3.46 mm). From the scan data, a thickness of the retinal NFL around the scanned circle is measured. However, optic disc sizes vary from patient to patient. In order to utilize a fixed circle size for all patients, the circle diameter should be at least as large to encompass optic discs of all patients. Accordingly, the circle is arbitrarily sized large for most patients, which is not ideal as useful information, close to the optic disc, is missed in most patients. When utilizing circles with smaller diameters than the fixed size, however, the circle scans often clip the optic disc of some patients. Within the optic disc itself, NFL thickness cannot be measured. Accordingly, circle scans that cut into the optic disc can reduce efficacy of clinical and/or statistical analyses since data sets are excluded for arbitrary reasons, leading to bias in medical diagnoses.

In accordance with one embodiment, the neuropathy analysis apparatus 130 is configured to post-process image data 140 (and particular 3D scan data contained therein) to perform a simulated scan in an arbitrarily defined scan pattern. To illustrate further, this embodiment is described in accordance with an example in which the region of interest 112 includes a portion of the retina of the eye 110 centered on the optic disc. However, it is to be appreciated that the subject matter described herein is not limited to optic disc analysis and can be applied to other portions of the retina (e.g., macula) or any other anatomical structures of the eye in which diagnostically relevant patterns are observed.

To perform a simulated scan, for the purposes of glaucoma detection or monitoring, the neuropathy analysis apparatus 130 identifies the optic disc in the image data 140 and generates an optic disc mask. According to one example, the optic disc is identified via layer segmentation, or other image processing technique executed on the 3D scan data. In particular, the optic disc could be identified by discontinuity in the layer information. One known technique for identifying and masking the optic disc is called the Bruch's Membrane Opening (BMO) methodology, in which the Bruch's Membrane is conventionally interpreted to correspond to the distal retinal pigment epithelium (RPE) cell body boundary that is observed in retinal OCT images. In another example, the optic disc can be identified from other information included in image data 140, such as a fundus image. For instance, object recognition can be performed on the fundus image to generate the optic disc mask. Moreover, the optic disk mask can further be provided by a user, as part of input 132, to the neuropathy analysis apparatus. For instance, the optic disc can be manually drawn by the user on output images rendered from image data 140. In addition, it is to be appreciated that autonomously generate optic disc masks, generated either from the 3D scan data or fundus images, can be edited by the user.

When generated from the 3D scan data included in image data 140, the optic disc mask is a 3D volume that generally conforms to the optic disc or optic nerve head within the 3D volume represented by image data 140. For the arbitrarily defined scan pattern for the simulated scan, a substantially annular region, or a set of substantially annular sub-regions, is determined based at least in part on a size and shape of the optic disc mask. The substantially annular region can be any shape and/or size (e.g., diameter) relative to the optic disc mask ranging from a minimal fit where an inner dimension of the annular region correspond to a margin of the optic disc mask up to a maximum where the inner dimension of the annular region corresponds to a maximum dimension of the region of interest 112.

Figure 2:
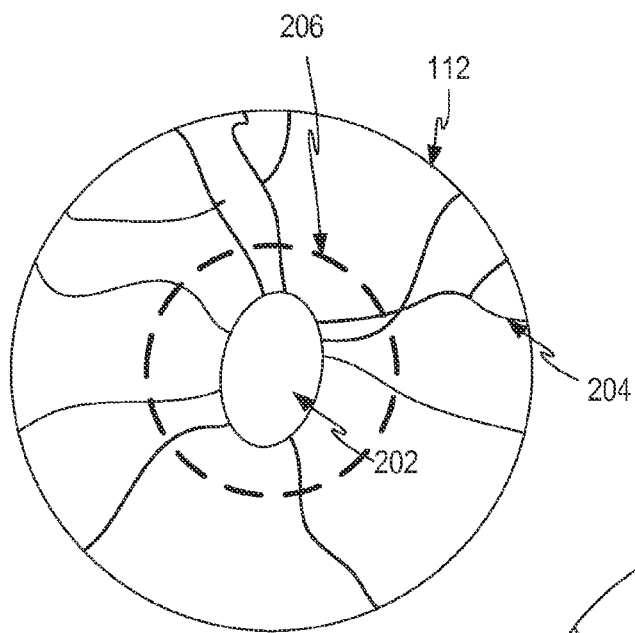
FIG. 2 illustrates a representation of an optic disc area of a retina of an eye and a conventional circle scan pattern overlay.
Figure 3:
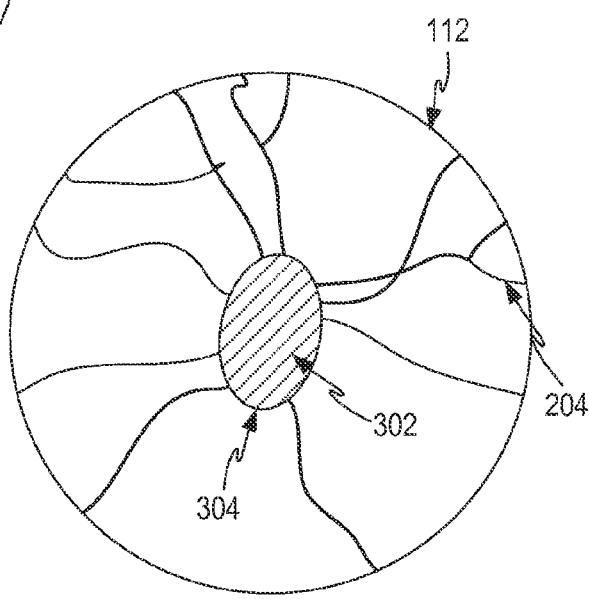
FIG. 3 illustrates a representation of an optic disc area of a retina of an eye overlaid with an optic disc mask.

To illustrate the variable size and shape of the substantially annular region, FIG. 2 depicts a simplified representation of the region of interest 112, which is roughly centered on an optic disc 202. Also shown in FIG. 2, are various blood vessels 204, which may enter the retina via the optic disc 202 and a conventional circle scan path 206 corresponding to traditional circumpapillary scans. Once the optic disc 202 is identified and segmented in image data 140, an optic disc mask 302 having a margin or border 304 can be created as shown in FIG. 3. While shown as a two-dimensional (2D) mask for illustrative and descriptive purposes, it is to be appreciated that the optic disc mask is not limited to a 2D mask. As described above, the optic disc mask can be a 3D volume corresponding to portions of the entire 3D volume of the 3D scan data occupied by the optic disc, optic nerve head, and the optic nerve, for example.

Figure 4:
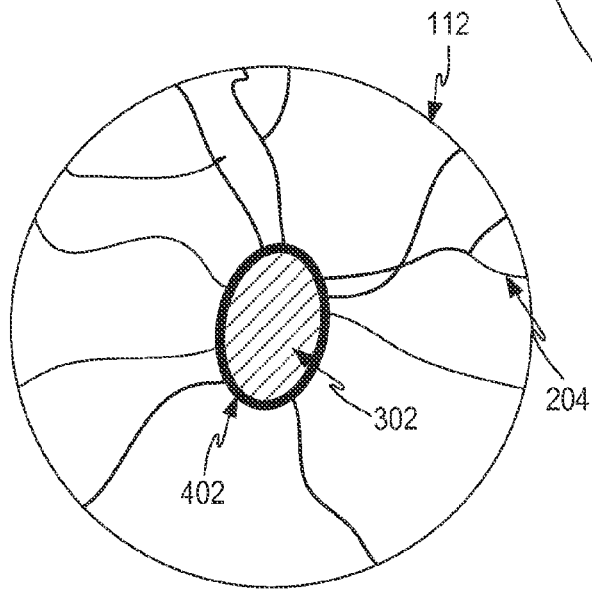
FIG. 4 illustrates a representation of an optic disc area of a retina of an eye with a minimally fitted annular region.
Figure 5:
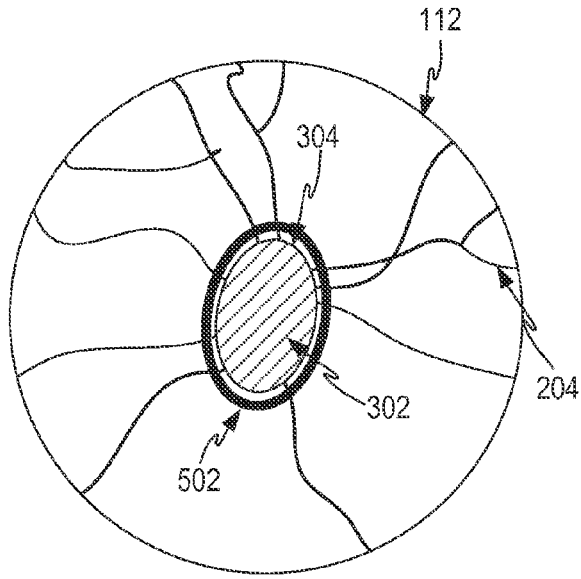
FIG. 5 illustrates a representation of an optic disc area of a retina of an eye with an arbitrarily sized annular region.

Based on the optic disc mask 302, a substantially annular region 402 is defined. FIG. 4, for example, depicts a minimal fit for the annular region 402 which substantially corresponds to margin 304 of the optic disc mask 302. That is, an inner dimension of the substantially annular region 402 is approximately the same as a dimension of the margin 304. FIG. 5 depicts another example annular region 502 having an inner dimension greater than the dimension of the margin 304.

Figure 6:
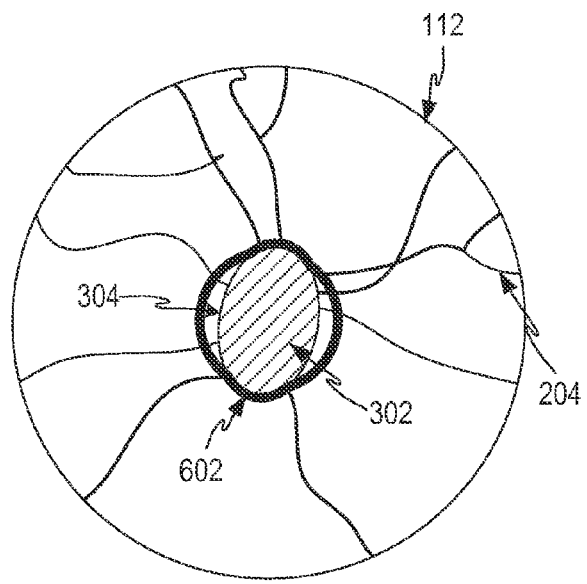
FIG. 6 illustrates a representation of an optic disc area of a retina of an eye with a hybrid annular region.

FIG. 6 illustrates yet another technique to derive an annular region 602. In this example, the annular region 602 can be referred to as a hybrid shape. The hybrid shape is determined by taking a first shape (e.g., a circle, an ellipse, or any other arbitrary shape) having an arbitrarily sized dimension (e.g., arbitrarily sized diameter in case of a circle) and centering the first shape on the optic disc mask 302. The first shape can be combined, i.e., merged, with a generated annular region such as the minimal fit annular shape to generate the annular region 602. For instance, in terms of polar coordinates where the origin is the center of the optic disc mask 302, an r value for the inner dimension of the annular region 602 can be determined as a maximum between an inner dimension of the minimal fit annular shape and an inner dimension of the first shape, for each θ.

Yet another technique for generating the substantially annular region could involve calculating the annular region using a formula that is a function of the polar angle θ and the outer boundary of the optic disk mask. However, it is to be appreciated that other merge techniques can be applied provided that the resultant annular region 602 does not cut into the optic disc mask 302.

Figure 7:
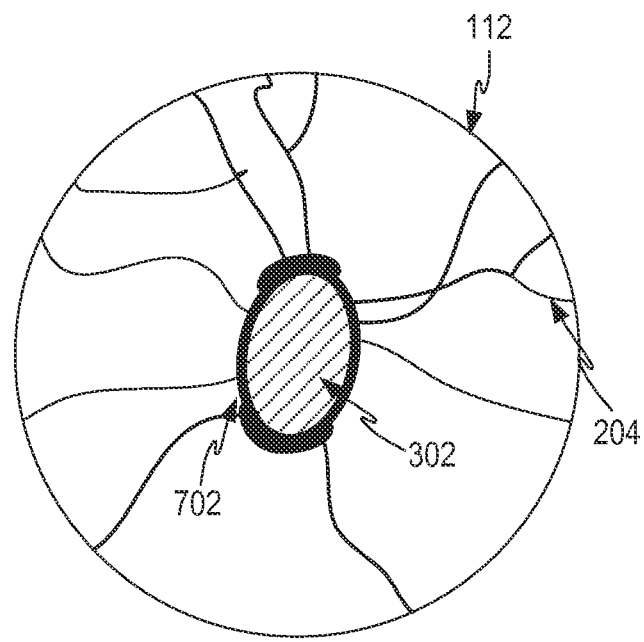
FIG. 7 illustrates a representation of an optic disc area of a retina of an eye with an annular region having a variable width.

In addition to shape and size of the annular region, it is to be appreciated that a width of the annular region is also variable. Width, in this instance, refers to a difference between the outer dimension of the annular region and the inner dimension of the annular region. The width can be user-definable, e.g. by input 132, or established by the neuropathy analysis apparatus 130. Moreover, just as the shape and size of the annular region can be internally variable, i.e. the shape and size can change within a particular region such as annular region 602, so can the width. For instance, given the typical arcuate pattern of thinning associated with glaucoma, the width of the annular region can be greater within the arcuates such as annular region 702 shown in FIG. 7.

Figure 8:
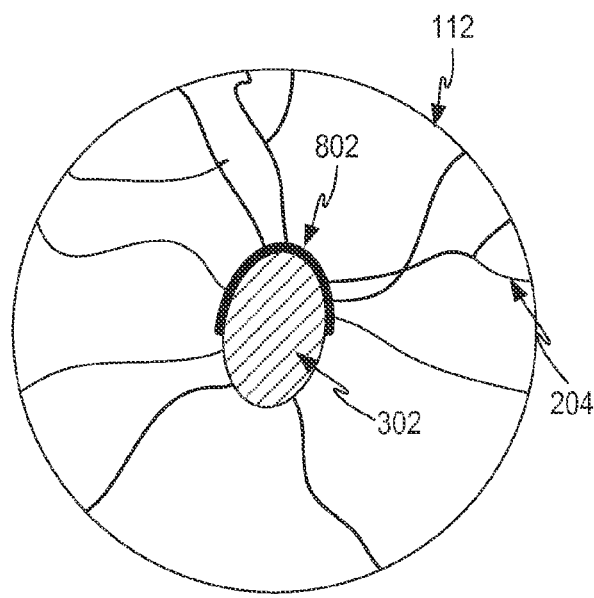
FIG. 8 illustrates a representation of an optic disc area of a retina of an eye with an annular sub-region.
Figure 9:
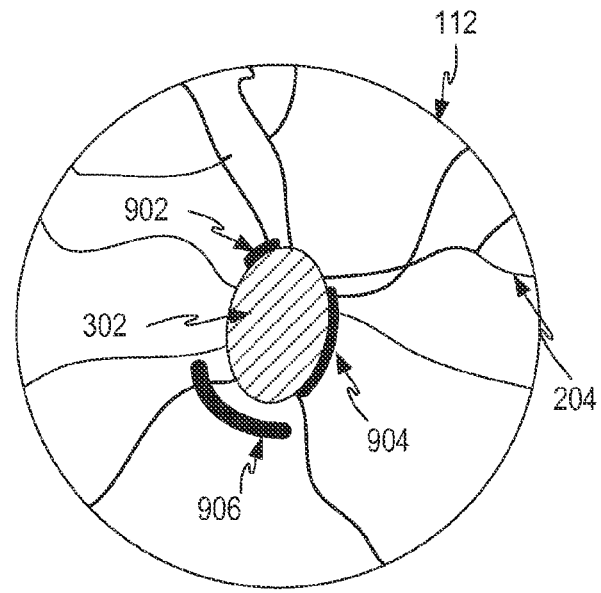
FIG. 9 illustrates a representation of an optic disc area of a retina of an eye with a plurality of annular sub-regions.

Moreover, the annular region subject to the simulated scan can be a discontinuous region formed from one or more sub-regions. FIG. 8 illustrates an example annular sub-region 802 spanning a superior hemisphere of the optic disc mask 302. In addition to hemispheres, sub-regions can be defined in terms of temporal, nasal, superior, and inferior quadrants; in terms of 45° shifted quadrants (e.g., temporal-superior quadrant); in terms of clock hours (e.g., 1 o'clock, 6 o'clock, etc.), or the like. Further, as shown in FIG. 9, sub-regions can have arbitrary sizes, shapes, and widths as illustrated by sub-regions 902, 904, and 906. Similar to the width described above, the shapes, sizes, and number of sub-regions can be user-definable, e.g. by input 132, and/or set autonomously by the neuropathy analysis apparatus 130.

Once the annular region is determined, neuropathy analysis apparatus 130 performs the simulated scan. In a simulated scan, a portion of image data 140 corresponding to the annular region is extracted. The portion of image data 140 extracted can be, for example, respective A-scans for locations within the annular region. From the A-scans, a simulated B-scan can be constructed or interpolated representing a cross-section along the annular region. In another example, the simulated B-scan can be constructed or interpolated from the 3D scan data of the image data 140.

After the simulated scan, i.e., after image data corresponding to the annular region is extracted, various measurements can be aggregated and/or integrated over the annular region. Aggregation can involve summation, averaging, taking a quintile, etc. of a collection of measurement values within the annular region. According to one example, measurements can be initially acquired prior to optic disc masking and/or determination of the annular region. For instance, during segmentation of image data 140, layer boundaries can be identified within image frames and layer thickness measurements are obtained. In another example, measurements can be acquired from A-scans corresponding to the annular region after execution of the simulated scan.

In one example, measurements can include layer thicknesses of individual layers (e.g., NFL, GCL, etc.), of combinations of layers (e.g., GCL and inner plexiform layer (GCL+); NFL, GCL, and IPL (GCC), etc.), or of all retinal layers. In another example, measurements can include attenuation coefficients (i.e., a measure of a degree to which light attenuates while passing through a layer), integrated attenuation coefficients, or other image-derived coefficient measures (e.g., polarization, possibly measured by polarization sensitive OCT; image intensity; image magnitude, etc.). Further, the measurements can include atrophic measures referring to a determination of a percentage of area within the annular region in which peripapillary atrophy is observable. Atrophic areas can be identified as areas in which a Bruch's membrane is intact while one or more of the following conditions also exist: a) lack of definition of delineation within inner retinal layers, b) absence of either an inner segment/outer segment junction (IS/OS) and/or a retinal pigment epithelium (RPE), or c) excessive brightness of choroid tissue within OCT image data. Alternatively, atrophic areas can be identified by locating areas having any one of the above-noted criteria without further restriction by the Bruch's membrane constraint.

Neuropathy analysis apparatus 130 can utilize normative databases to facilitate identification of optic neuropathies from the measurements aggregated and/or integrated over the annular region. Thus, comparison results to the normative databases, the simulated B-scan, a generated 3D volume corresponding to a volume of the annular region, measurement values, summary statistics (e.g., mean, median, standard deviation, etc.) of measurement values, image data 140 or portion thereof, can all be combined in total or in part to generate analysis results 134 for display and/or further analysis.

For example, analysis results 134 can include display data representing the simulated B-scan derived from the annular region. The simulated B-scan can be accompanied by measurement results and typical red/yellow/green normative analysis results. In another example, measurement results can be represented (visually, graphically, numerically, etc.) as overlays with an OCT-derived map, such as a thickness map, projection image, etc., or an image acquired from an alternative modality (e.g., scanning laser ophthalmoscopy, fundus camera, etc.).

In another embodiment, imaging apparatus 120 and neuropathy analysis apparatus 130 can be configured to directly scan the annular region. Imaging apparatus 120, or other apparatus (not shown), can acquire a preliminary image such as a fundus image or an OCT fundus image. From the preliminary image, the optic disc is identified and a suitable mask generated. From the mask, an annular region is defined in scan control input 150 provided to the imaging apparatus 120 to enable direct scanning of the annular region. Imaging apparatus 120 can further obtain secondary imaging in order to correct rapid eye movement while scanning the annular region.

While the aspects above were discussed with respect to optic disc scans, it is to be appreciated that the techniques described herein can be applied to other anatomical areas. For instance, as mentioned above, some optic neuropathies can present as atrophy in the GCL (or GCL+) "doughnut" around the macula. The fovea, i.e., the center of the macula, is not included in the "doughnut". Accordingly, OCT scan data of the macular region can be similarly analyzed as described above to identify the fovea, generate a suitable mask, and determine an annular region substantially surrounding the mask. In this regard, the "doughnut" shape around the macula can be isolated to acquire focused measurement results. Moreover, it is to be appreciated that image data 140 can include 3D scan data of both the macular region and the optic disc region. In this example, an optic disc mask and a fovea mask can be generated as well as two substantially annular region respectively fitted based on the optic disc mask and the fovea mask. Accordingly, conditions of the tissues around the optic disc and the macular region can be measured and analyzed together. It should be appreciated, however, that the measurements for the optic disc region and for the macular region are not necessarily the same measurement (although they can be). Accordingly, it may be useful to measure them separately. For example, it may be desirable to measure NFL characteristics around the optic disc and to measure the ganglion cell characteristics in the macular region.

Figure 10:
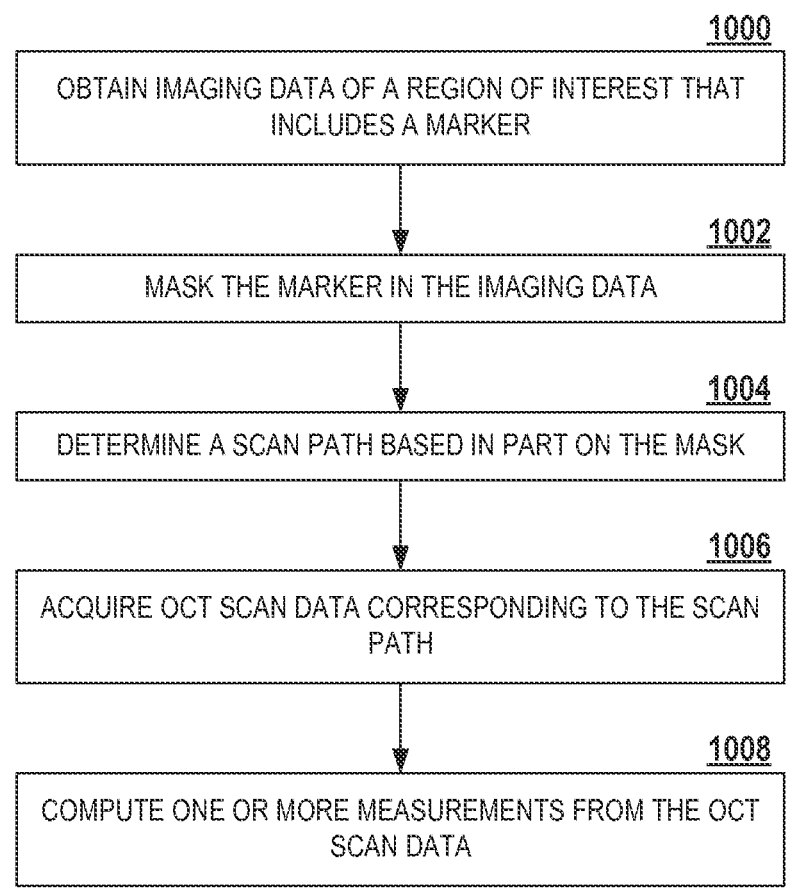
FIG. 10 is a flow diagram of an exemplary, non-limiting embodiment for detecting optic neuropathies.

Referring to FIG. 10, illustrated is an exemplary, non-limiting method for detecting optic neuropathies with OCT. This method can be implemented, for example, by system 100 described above. At 1000, imaging data of a region of interest that includes a marker is obtained. The imaging data can be acquired by an OCT imaging apparatus or by another imaging modality. In an example, the region of interest can be a retina of an eye and the marker can be an anatomical feature such as an optic disc or a fovea. At 1002, the marker is masked in the imaging data. At 1004, a scan path is determined in part on the mask. For instance, the scan path can traverse at least a portion of a region enclosing the mask, and at least partially fitted to the mask. For example, the region can be a minimally fitted region such that an inner dimension of the region corresponds to an outer dimension of the margin or border of the mask. At 1006, OCT scan data corresponding to the scan path is acquired. The OCT scan data can be acquired directly, i.e., by actually scanning the scan path with the imaging apparatus, or virtually, i.e., by a simulated scan. At 1008, one or more measurements can be computed from the OCT scan data and further analyzed to detect optic neuropathies. As described previously, measurements can include thickness measurements of one or more retinal layers, attenuation-based measurements, image-derived coefficients, atrophic measures, and the like.

Figure 11:
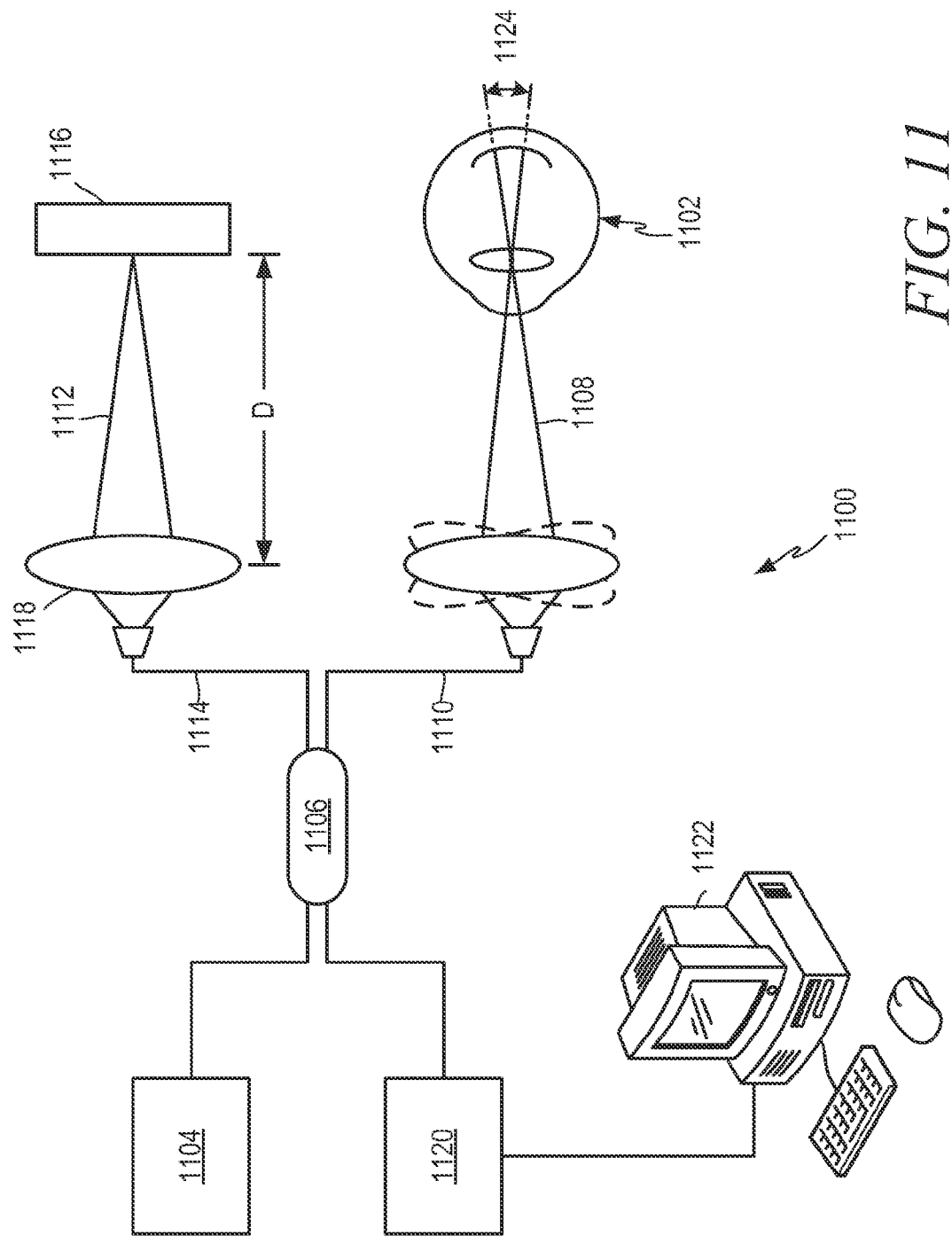
FIG. 11 illustrates a schematic diagram of an exemplary, non-limiting optical coherence tomography system in which one or more aspects of various embodiments herein can be implemented.

Turning to FIG. 11, illustrated is an exemplary, non-limiting embodiment of an optical coherence tomography (OCT) system 1100 in which one or more aspects described above can be implemented. As shown, system 1100 can perform an imaging technique used in ophthalmology to generate cross-sectional images of portions of an eye 1102, such as the retina for example.

Generally, OCT involves impinging light from a low-coherence broadband light source 1104 onto portions of the eye 1102, and observing reflected light to generate a cross-sectional image of those portions of the eye 1102. Light from the light source 1104 is split by a an optical adaptor 1106 such as a beam splitter, fiber coupler or the like, into two portions: a sample portion 1108 that travels along a path 1110 toward the eye 1102, and a reference portion 1112 that travels along a path 1114 toward a reference reflector such as a mirror 1116. The sample portion 1108 and the reference portion 1112 are at least partially reflected, and the reflected portions combined by the optical adaptor 1106 and the intensity or other quality of the combined, reflected light is sensed by a detector 1120 operatively connected to transmit a signal indicative of the sensed quality to be received by a computer 1122. When the distance traveled by the sample portion 1108 is within a coherence length of the distance traveled by the reference portion 1112, an optical interference pattern is created, affecting the intensity of the reflected and combined light. The intensity of the combined, reflected light varies depending upon the properties (e.g., tissue backscattering, polarization, etc. . . . ) of the portions of the eye 1102 that are illuminated by the sample portion 1108. Information about such properties of the illuminated portion of the eye 1102 can then be determined based on the intensity of the combined, reflected light, and used to generate image data pertaining to that illuminated portion of the eye 1102.

The depth to which the sample portion 1108 penetrates the eye 1102 can be controlled in the time domain by varying a distance D separating a transmitter 1118 of the reference portion 1112 from the mirror 1116. Alternatively, the depth of penetration can be controlled in the frequency domain by utilizing a broadband light source or alternatively sweeping the wavelength of the light source 1104 over a range of frequencies, optionally in combination with varying a distance D separating a transmitter 1118 of the reference portion 1112 from the mirror 1116. Conducting a Fourier analysis on the combined, reflected light relates the light reflected at different frequencies to light reflected at different depths of the eye 1108. As noted above, the distance D may optionally be varied even when depth is controlled in the frequency domain. This can be done, for example, to counterbalance saccadic eye movements, or to counterbalance gradients associated with eye shape. Further, in a 3D scan, due to eye shape and curvature, certain retinal locations are closer to the pupil than others. Therefore, it may also be necessary to alter the distance D in order to stay within the coherence window even in Fourier domain scans.

The sample portion 1108 having a fixed penetration depth can be reflected through adjustment of a mirror, lens, etc. . . . , to various different orientations (illustrated using broken lines in FIG. 11) to illuminate different spatial locations over a region of interest 1124 (e.g., macula, optic disc, etc. . . . ) within the eye 1102. The intensity of the combined, reflected light (or other quality) sensed by the detector 1120 is transmitted to the computer 1122 shown in FIG. 1 for each different spatial location of the region of interest 1124. The computer 1122, which includes a processor for executing computer-executable instructions stored by a non-transitory, computer-readable medium such as a hard drive, for example, stores OCT image data, the sensed intensities and/or other values related to the intensities, such as the calculated depth, in a database also stored on the hard drive or on some other non-transitory computer-readable medium such as random access memory (RAM) or the like. The database can be structured to store each value of the intensity sensed by the detector 1120 with a link or other relationship to the respective different spatial location in the region of interest 1124 from which the corresponding light was reflected. Similarly, the intensity values of light reflected from the different spatial locations, but for a different axial penetration depth of the sample portion 1108 of the light into the region of interest 1124, can be stored in a separate array. The data in the plurality of arrays can collectively be utilized by the computer 1122 to generate a B-scan, for example.

Computer 1122 can include additional software and/or computer-executable code to process intensity data and generate, for example, image data 140 from FIG. 1. In addition, computer 1122 can include computer-executable instructions to carry out the functions of the neuropathy analysis apparatus 130 described above. In this regard, the neuropathy analysis apparatus 130 and the imaging apparatus 120 in FIG. 1 can be implemented by system 1100 or other similarly constructed system.

Figure 12:
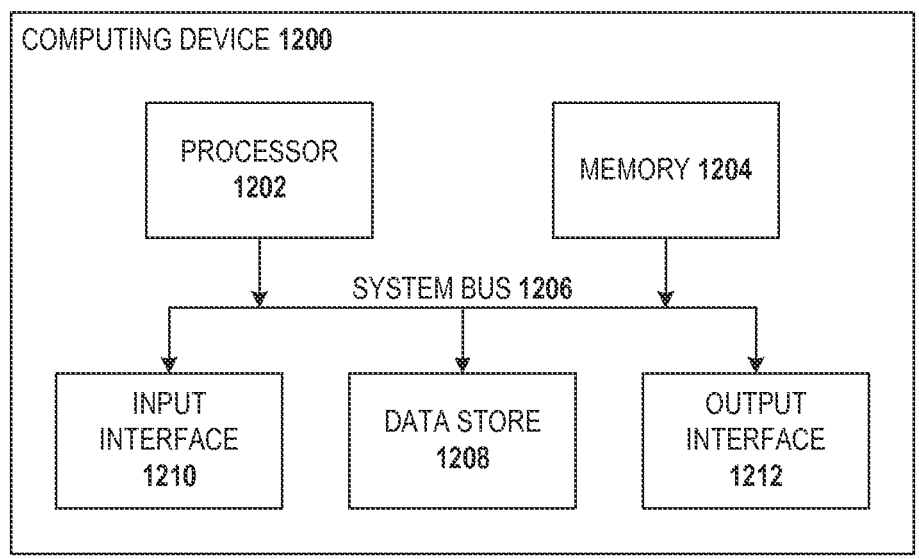
FIG. 12 illustrates a block diagram of an exemplary, non-limiting computing device or operating environment in which one or more aspects of various embodiments described herein can be implemented.

Referring now to FIG. 12, a high-level illustration of an exemplary computing device 1200 that can be used in accordance with the systems and methodologies disclosed herein is illustrated. The computing device 1200 includes at least one processor 1202 that executes instructions that are stored in a memory 1204. The instructions may be, for instance, instructions for implementing functionality described as being carried out by one or more components discussed above or instructions for implementing one or more of the methods described above. The processor 1202 may access the memory 1204 by way of a system bus 1206.

The computing device 1000 additionally includes a data store 1208 that is accessible by the processor 1202 by way of the system bus 1206. The computing device 1200 also includes an input interface 1210 that allows external devices to communicate with the computing device 1200. For instance, the input interface 1210 may be used to receive instructions from an external computer device, from a user, etc. The computing device 1200 also includes an output interface 1212 that interfaces the computing device 1200 with one or more external devices. For example, the computing device 1200 may display text, images, etc. by way of the output interface 1212.

Additionally, while illustrated as a single system, it is to be understood that the computing device 1200 may be a distributed system. Thus, for instance, several devices may be in communication by way of a network connection and may collectively perform tasks described as being performed by the computing device 1200.

Moreover, the acts described herein may be computer-executable instructions that can be implemented by one or more processors and/or stored on a computer-readable storage medium or media. The computer-executable instructions can include a routine, a sub-routine, programs, a thread of execution, and/or the like. Still further, results of acts of the methodologies can be stored in a computer-readable storage medium, displayed on a display device, and/or the like.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the term "exemplary" is intended to mean "serving as an illustration or example of something."

Various functions described herein can be implemented in hardware, software, or any combination thereof. If implemented in software, the functions can be stored on or transmitted over as one or more instructions or code on a computer-readable medium. Computer-readable media includes both computer-readable storage media and communication media including any medium that facilitates transfer of a computer program from one place to another. A computer-readable storage media can be any available media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Also, a connection can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Illustrative embodiments have been described, hereinabove. It will be apparent to those skilled in the art that the above devices and methods may incorporate changes and modifications without departing from the general scope of the claimed subject matter. It is intended to include all such modifications and alterations within the scope of the claimed subject matter. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for optical coherence tomography (OCT) imaging, comprising:
   obtaining first data comprising ophthalmic imaging data of a region of interest of a subject, the region of interest including at least one anatomical marker;
   generating an anatomical mask of the anatomical marker based on the imaging data by using a processor to execute an image processing technique;
   determining a scan path based at least in part on the mask, the scan path traversing at least a portion of an arbitrary enclosing shape at least partially fitted around the mask; and
   acquiring second data comprising three-dimensional (3D) OCT scan data corresponding to the scan path.

2. The method of claim 1, wherein acquiring the 3D OCT scan data corresponding to the scan path further comprises directly scanning the scan path with an OCT imaging apparatus.

3. The method of claim 1, wherein obtaining the imaging data further comprises performing a 3D OCT scan of the region of interest including the anatomical marker.

4. The method of claim 1, wherein acquiring the 3D OCT scan data corresponding to the scan path further comprises performing a simulated scan of 3D OCT scan data of the region of interest including the anatomical marker.

5. The method of claim 4, wherein performing the simulated scan comprises extracting data from the 3D OCT scan data within the scan path.

6. The method of claim 5, wherein the data extracted are a plurality of A-scans from the 3D OCT scan data within an area of the region of interest covered by the scan path.

7. The method of claim 6, further comprising generating a simulated B-scan from the plurality of A-scans.

8. The method of claim 1, further comprising acquiring at least one measurement from the 3D OCT scan data corresponding to the scan path.

9. The method of claim 8, wherein the measurement comprises at least one of a layer thickness, an attenuation coefficient, an image-derived coefficient or a combination thereof.

10. The method of claim 8, wherein the region of interest is a retina and the anatomical marker is an optic disc, and
acquiring the at least one measurement comprises measuring a characteristic of at least a nerve fiber layer of the retina within the scan path.

11. The method of claim 8, wherein the region of interest is a retina and the anatomical marker is a fovea, and
acquiring the at least one measurement comprises measuring a characteristic of a ganglion cell layer of the retina within the scan path.

12. The method of claim 8, wherein the region of interest is a retina, and
acquiring the at least one measurement comprises measuring the characteristic over one layer or a combination of layers of retina, the one layer or combination of layers including at least one of:
a ganglion cell layer (GCL);
an inner plexiform layer (IPL);
a nerve fiber layer (NFL);
a combination of the GCL and the IPL;
a combination of the NFL, the GCL, and the IPL; or
all retinal layers.

13. The method of claim 8, wherein the measurement is an atrophic measure indicating a percentage of an area of the scan path in which peripapillary atrophy is detected.

14. The method of claim 8, further comprising displaying information derived from at least one of the at least one measurement, the imaging data, or the 3D OCT scan data.

15. The method of claim 14, wherein displaying the information comprises displaying a visual representation of measurement results as an overlay on an OCT-derived image.

16. The method of claim 8, further comprising comparing the at least one measurement to a normative database.

17. The method of claim 1, wherein the arbitrary enclosing shape is a substantially annular shape.

18. The method of claim 17, wherein an inner dimension of the substantially annular shape corresponds to a margin of the mask.

19. The method of claim 17, wherein the scan path comprises one or more sub-sections of the substantially annular shape.

20. The method of claim 19, wherein the one or more sub-sections are discontinuous.

21. The method of claim 1, wherein determining the scan path further comprises selecting a first enclosing shape, aligning the first enclosing shape with the mask, and adjusting at least one dimension of the first enclosing shape such that a minimum value of the at least one dimension is greater than or equal a dimension of a margin of the mask.

22. A method for detecting optic neuropathies from optical coherence tomography (OCT) imaging data, comprising:
acquiring first data comprising ophthalmic imaging data of a region of a retina that includes an optic disc;
determining an optic disc mask based on the imaging data by using a processor to execute an image processing technique;
determining a scan path based at least in part on the optic disc mask, wherein the scan path comprises one or more sub-paths, the one or more sub-paths being positioned based in part on an outer dimension of the optic disc mask; and
acquiring second data comprising three-dimensional (3D) OCT scan data corresponding to the scan path.

23. The method of claim 22, wherein obtaining the imaging data further comprises performing a 3D OCT scan of the region of the retina including the optic disc.

24. The method of claim 23, wherein acquiring the 3D OCT scan data corresponding to the scan path further comprises performing a simulated scan from results of the 3D OCT scan of the region of the retina including the optic disc.

25. The method of claim 22, further comprising acquiring at least one measurement value from the 3D OCT scan data corresponding to the scan path.

26. The method of claim 22, further comprising displaying information derived from at least one of the at least one measurement value, the imaging data, or the 3D OCT scan data.

27. The method of claim 22, wherein the one or more sub-paths traverse a minimally fitted annular shape having an inner dimension corresponding to the outer dimension of the optic disc mask.

28. An OCT imaging system, comprising:
an ophthalmic imaging apparatus for capturing OCT scan data of a region of interest of a subject, the region of interest including at least one anatomical marker;
a neuropathy analysis apparatus for processing the OCT scan data to output analysis results relevant to diagnosis of optic neuropathies,
wherein the neuropathy analysis apparatus is configured to:
generate an anatomical mask for the anatomical marker based on image processing of the OCT scan data by using a processor to execute an image processing technique,
determine a scan path based at least in part on the mask, the scan path traversing at least a portion of an arbitrary enclosing shape at least partially fitted around the mask,
extract portions of the OCT scan data corresponding to the scan path,
aggregate measurement values, relative to at least one characteristic of the region of interest, over the portions of the OCT scan data extracted, and
output, as the analysis results, information derived from at least one of the measurement values aggregated or the portions of the OCT scan data extracted.

29. The OCT imaging system of claim 28, wherein the neuropathy analysis apparatus is further configured to receive input, the input specifies at least one of:
a size and location of the arbitrary enclosing shape,
one or more sub-regions of the arbitrary enclosing shape included in the scan path, or
a width of the arbitrary enclosing shape.

30. The OCT imaging system of claim 28, wherein the neuropathy analysis apparatus is further configured to control the imaging apparatus to directly capture imaging data corresponding to the scan path.

31. The method of claim 1, wherein the 3D OCT scan data corresponding to the scan path is acquired from the imaging data of the region of interest of the subject.

32. The method of claim 22, wherein the 3D OCT scan data corresponding to the scan path is acquired from the imaging data of the region of the retina that includes the optic disc.

33. The method of claim 1, wherein the step of generating the mask is performed autonomously.

34. The method of claim 22, wherein the step of determining the optic disc mask is performed autonomously.

35. The method of claim 28, wherein the neuropathy analysis apparatus is configured to generate the mask autonomously.

* * * * *